US00PP09941P

United States Patent [19]

Jessel, Jr.

[11] Patent Number: Plant 9,941

[45] Date of Patent: Jul. 1, 1997

[54] CARNATION PLANT VARIETY NAMED 'CFPC WHITE SCULPTURE'

[75] Inventor: Walter H. Jessel, Jr., Gonzales, Calif.

[73] Assignee: California Florida Plant Co., L.P., Salinas, Calif.

[21] Appl. No.: 626,478

[22] Filed: Apr. 2, 1996

[51] Int. Cl.[6] ..... A01H 5/00

[52] U.S. Cl. ..... Plt./70.3

[58] Field of Search ..... Plt./70.2, 70.3

*Primary Examiner*—Howard J. Locker

*Attorney, Agent, or Firm*—Christie, Parker & Hale, LLP

[57] ABSTRACT

A new variety of carnation plant providing sprays of small white flowers which do not discolor in low light periods.

1 Drawing Sheet

SUMMARY OF THE INVENTION

The present invention relates to a new and distinct variety of carnation plant which was originated by me in a controlled breeding program by my crossing as seed parent the variety known as 'Koreno' and as pollen parent an unnamed and unpatented seedling of my creation identified as No. 890092. The varietal denomination of this new carnation is 'CFPC White Sculpture'.

Among the novel combination of characteristics possessed by the new variety which distinguishes it are resistance to soil-borne disease such as *Fusarium oxysporum*, and *F. graminearum* and root-rots such as damping off, water molds and the like; small size spray flowers which open fully without bursting the calyx and causing "splits", and a very vigorous and free-breaking plant habit with strong straight stems. Flowers of the new variety also display no flower color "tinging" or discoloration under low temperatures.

Asexual reproduction by propagation by side shoot cuttings of the new variety as performed in Salinas, Calif., shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Colour Chart (RHSCC). The terminology used in color description herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Where terms such as average, normal, ordinary, etc., are used, the characteristics so described are not considered distinguishing.

Name: 'CFPC White Sculpture'.

Classification:

*Botanical.*—Hybrid, Dianthus caryophyllus.

*Commercial.*—Carnation, spray-type.

Parentage:

*Female parent.*—'Koreno'.

*Male parent.*—Unnamed seedling (No. 890092).

1. Plant
   - *Height.*—About 44 to 45 inches.
   - *Growing habit.*—Herbaceous, upright.
   - *Blooming habit.*—As a spray.
   - *Breaking action.*—Excellent.
   - *Rooting time.*—About 18 days.
   - *Mutation prone.*—No.
   - *Disease resistance.*—Good.
2. Foliage:
   - *Color.*—Upper side: Near 136B. Lower side: Near 137A.
   - *Size.*—About 6½ inches long and about ¼ to ⅜ inches wide.
   - *Quantity.*—Numerous.
   - *Shape.*—Lanceolate.
   - *Texture.*—Smooth.
   - *Ribs.*—Central, Keeled.
   - *Arrangement.*—Bi-Lateral along stem.
   - *Stem color.*—Green.
3. Bud:
   - *Shape.*—Oval.
   - *Color.*—Green.
   - *Length.*—About ¾ inch.
   - *Diameter.*—About ⅝ inch.
4. Calyx:
   - *Numbers of sepals.*—About 5.
   - *Length.*—About 1 inch.
   - *Width.*—About ⅜ inch.
   - Color: Outside — near 137B. Inside — near 139D.
5. Bloom:
   - *Shape.*—Round.
   - *Size.*—Diameter average: About 1⅝ to 1¾ inches. Depth average: About 1 inch.
   - *Borne.*—Terminal as a spray.
   - *Color.*—General tonality: White. Upper side: Whiter than near 155D. Lower side: Whiter than near 155D. Center: Whiter than near 155D. Outer petals: Whiter than near 155D.
   - *Keeping quality.*—Good.
   - *Fragrance.*—Slight.
6. Petals
   - *Number.*—About 24.

*Outer petals.*—Length: About 1⅝ inch. Width: About 1 inch.

*Central petals.*—Length: About 1½ inch. Width: About ⅔ inch.

*Texture.*—Smooth.

*Form.*—Fan shaped.

*Appearance.*—Shiny.

7. Reproductive organs:

*Stamens.*—About 6 to 8; arranged around ovary.

*Anthers.*—Length — about ⅛ inch; light tan length — about ½ to ¾ inches; white.

*Pistil.*—Number: About 2. Color: White. Length: About ⅝ inch.

*Stigma.*—Number: About 2. Color: White.

*Ovary.*—Shape: Conical. Color: Body — green. Apex — tan.

*Fertility.*—Female: Average. Male: Good.

I claim:

1. A new and distinct variety of carnation plant substantially as shown and described.

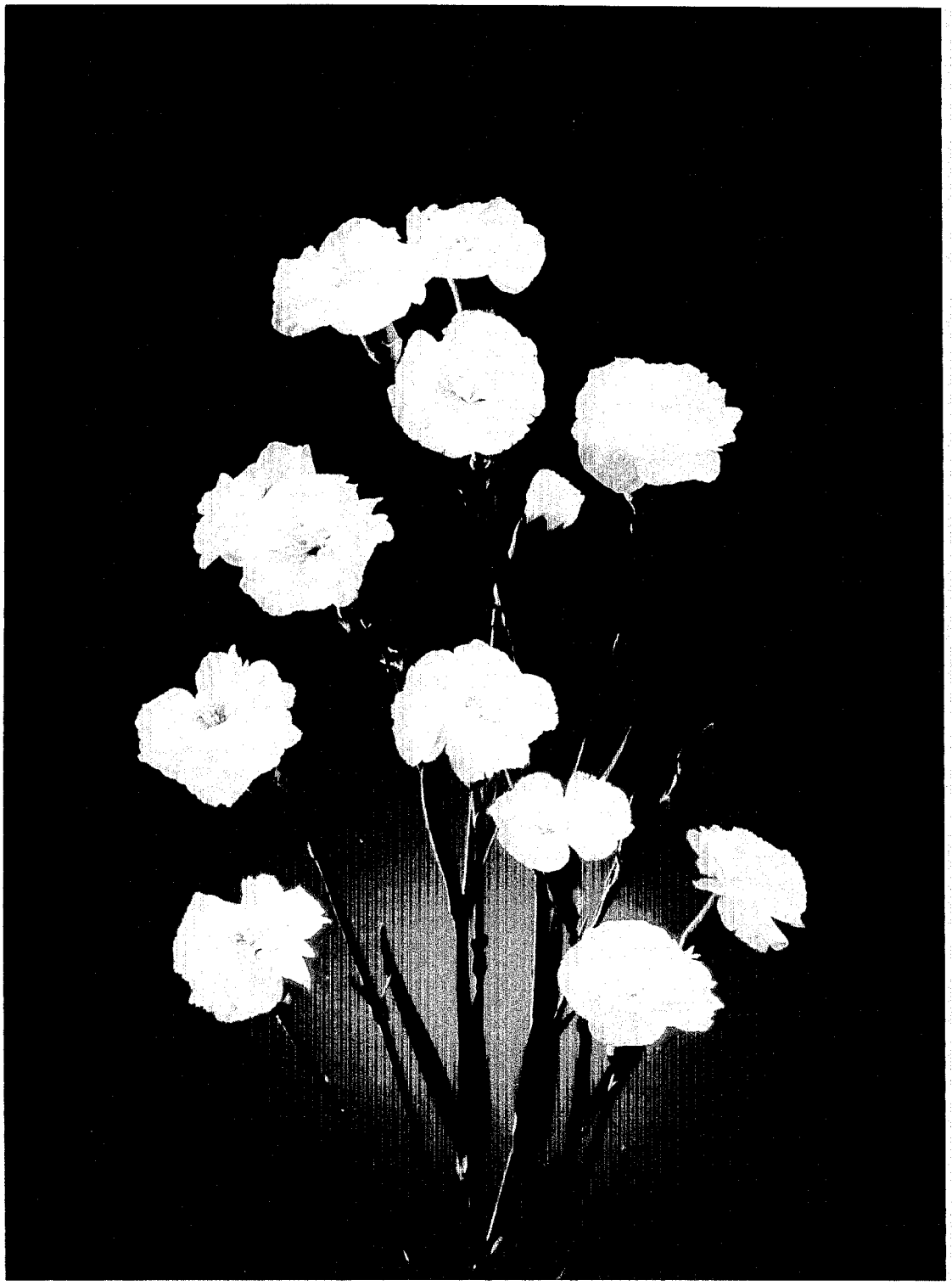

* * * * *